(12) United States Patent
Platts

(10) Patent No.: US 6,440,438 B2
(45) Date of Patent: *Aug. 27, 2002

(54) COVERING IMPREGNATED WITH INSECTICIDE

(75) Inventor: Lynda Margaret Platts, Gloucestershire (GB)

(73) Assignee: Protec Health International Limited, Gloucestershire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,857

(22) Filed: Oct. 23, 1998

(30) Foreign Application Priority Data

Oct. 24, 1997 (GB) .............................. 9722578

(51) Int. Cl.⁷ ..................... A01N 25/34; A01N 25/00; A01N 25/08
(52) U.S. Cl. ..................... 424/403; 424/405; 424/409; 424/411
(58) Field of Search ................ 424/405, 403, 424/453, 409, 411, 443; 8/115.02, 115.62

(56) References Cited

U.S. PATENT DOCUMENTS

| 5,198,287 A | * | 3/1993 | Samson | 428/248 |
| 5,238,682 A | * | 8/1993 | Akasaka et al. | 424/409 |
| 5,487,861 A | * | 1/1996 | Reeder et al. | 264/134 |
| 5,916,580 A | * | 6/1999 | Shober et al. | 424/405 |

FOREIGN PATENT DOCUMENTS

| JP | 8-245324 | 9/1996 | |
| WO | WO 96/28974 | 9/1996 | .......... A01N/25/34 |
| WO | WO 97/24484 | 7/1997 | |

OTHER PUBLICATIONS

Burr, M. L. et al., "Prevention of mite infestation of bedding by means of an impregnated sheet," *Allergt,* vol. 43, 1988, pp. 299–302.

* cited by examiner

*Primary Examiner*—Russell Travers
*Assistant Examiner*—Shengjun Wang
(74) *Attorney, Agent, or Firm*—Stroock & Stroock & Lavan LLP

(57) ABSTRACT

A covering for soft furnishing is impregnated with an insecticide, such as permethrin. The concentration of permethrin is sufficient to kill house dust mites and deter larger insects such as fleas and ticks. The insecticide is released from the covering over an operational period so as to encourage the absorption of the insecticide into surrounding soft furnishings. The covering is manufactured from machined fabric, such as knitted voile, having interstices sufficiently small to reduce the rate of insecticide release over the operational period.

6 Claims, 5 Drawing Sheets

COVERING IMPREGNATED WITH INSECTICIDE

This application claims foreign priority of Great Britian application 9722578.3, filed Oct. 24, 1997.

FIELD OF THE INVENTION

The present invention relates to coverings impregnated with insecticide for soft furnishings. In particular, the invention relates to coverings impregnated with insecticide, wherein the insecticide is released from the covering over an operational period.

BACKGROUND OF THE INVENTION

Dust mites live in substantial numbers in places offering warm, humid conditions and a supply of human skin scales and other debris upon which they feed. The surface of a mattress is a particularly attractive habitat and it is understood that the mites move significant distances on and within mattresses in order to seek out and to remain within optimal environmental conditions. The World Health Organisation has identified dust mite concentrations at which genetically predisposed individuals develop antibodies to the house dust mite allergen and concentrations at which there are risks of acute asthma attacks in mite-allergic patients. Thus, it is possible to perform an examination of soft furnishings, such as beds, used by an allergic individual to determine concentrations of house dust mites and to take appropriate action in order to reduce or eliminate these concentrations.

When a permethrin impregnated mattress cover is fitted to a bed, the permethrin formation comes into intimate contact with the surface and sides of the mattress. This close contact, together with the pressure of the occupant of the bed, causes some of the permethrin to move onto the surface of the mattress itself and then subsequently into the surface layers of the mattress. The texture of the mattress cover, in combination with movement between the cover and mattress, results in the permethrin being distributed relatively uniformly within the mattress itself. As the mites move within the mattress, most of them will eventually come into contact with this relatively uniform and continuous zone of permethrin impregnated fabric resulting in the absorption of the chemical into the mite's body.

Permethrin that has become absorbed or deposited on the mite's foodstuff may become ingested allowing it to enter into the haemolymph. In addition, while the mite is in physical contact with deposits of permethrin, small quantities of the chemical adhere to the mite resulting in diffusion onto the surface of the mite's cuticle. Once on the cuticle, the permethrin diffuses directly through the cuticular layers and thereafter passes into the mite's haemolymph. Once in the haemolymph, the chemical becomes absorbed by the haemolymph lipoproteins resulting in subsequent transportation to the site of action. In addition, permethrin may also diffuse laterally along the trachea of the mite, thereby resulting in it being passed directly to the mite's nervous system.

The presence of permethrin within the mite's nervous system results in an increase in the extent to which sodium ions diffuse into the axon of the nerves, resulting in depolarisation. This in turn results in either a spontaneous nerve firing or in the blocking of further action potentials passing along the nerve fibre. The end result of these processes is a disruption in the passage of nervous impulses along the nerve causing either muscular excitation or paralysis, depending upon the stage of the intoxication process.

Disruption of co-ordinated muscle control does not by itself lead directly to the death of the mites but once this control has been lost, a finite period of time will elapse until an essential life sustaining process becomes sufficiently deranged to result in the death of the mite. Thus, a common cause of mite death due to the presence of permethrin is that of failure to control water balance, either internally or by an inability to seek a suitably humid environment.

Patent publication WO 96/28974 discloses the use of a netting impregnated with permethrin and fabricated into a cover appropriate for the covering of domestic articles such as mattresses and duvets etc. Tests in the laboratory suggests that a covering fabricated from the netting disclosed in the aforesaid patent publication should provide protection for a significant period of time when impregnated with a modest quantity of insecticide. However, field trials, conducted under more real life conditions, have shown that the duration over which a net cover provides adequate protection is significantly less than that anticipated by use in the laboratory. Furthermore, tests of this type have also shown that increasing the initial dose of insecticide does not significantly increase the active life of the covering in a proportional way. Furthermore, there is a limit to the extent to which any insecticide (such as permethrin) could be used in a health care situation.

Permethrin is not considered toxic to humans, however overexposure may lead to increased hypersensitivity to touch and sound, tremors and convulsions. Contact with permethrin may produce skin sensations such as numbing, burning or tingling but these are reversible and usually subside within a period of twelve hours. When placed directly in contact with the skin, tests have shown that about 0.5 percent of the chemical is absorbed by the skin, therefore care should be taken so as to minimise human exposure while maintaining the pesticide effect, as in any pesticide use.

It is an object of the present invention to increase the operational period over which a covering impregnated with insecticide is effective, without being required to increase initial insecticide concentrations.

SUMMARY OF THE INVENTION

According to a first aspect of the present invention, there is provided a covering for soft furnishing, impregnated with insecticide wherein said insecticide is released from said covering over an operational period so as to encourage the absorption of said insecticide into said soft furnishings, comprising a covering manufactured from machined fabric having interstices sufficiently small to reduce the rate of insecticide release over said operational period.

In a preferred embodiment, the covering is configured to be applied to mattresses, duvets, pillows or other bedding elements.

Preferably, the insecticide is a synthetic pyrethroid such as deltamethrin, sypermethrin, allethrin or bifenthrin and in a preferred embodiment the synthetic pyrethroid is permethrin.

In a preferred embodiment, the fabric is machined from polyester yarn, preferably having a gauge in the range of twenty to one hundred decitex. Preferably the interstices of the fabric are smaller than that provided by machined netting and in a preferred embodiment, the machined fabric is a knitted voile. Preferably, the knitted voile has a weight of between thirty-five to forty-five grams per square meter and contains between four hundred to seven hundred milligrams of insecticide (preferably permethrin) per square meter.

According to a second aspect of the present invention, there is provided a covering for soft furnishings, impregnated with permethrin with a loading of between five hundred and six hundred milligrams per square meter and configured to release permethrin over an operational period of between one-and-a-half and two-and-a-half years to give a final loading of between one hundred to two hundred milligrams per square meter.

Preferably, the covering is fabricated totally or in part of knitted voile and said voile may be knitted from polyester yarn.

According to a third aspect of the present invention, there is provided a method of producing a covering for soft furnishings configured to provide protection against house dust mites, comprising the steps of knitting a voile from a polyester yarn; machining a cover from said knitted voile; and impregnating said machined cover with an insecticide.

In a preferred embodiment, the machined cover is impregnated by being immersed in an impregnation fluid and then rolled between rollers to control the level of fluid pick-up. Preferably, the rolled voile is passed through drying means to remove water from the insecticide.

In a preferred embodiment, the impregnation fluid is a suspension of permethrin in water and the impregnation fluid may be mixed by adding permethrin in organic solution to water to provide the required suspension. Preferably, the organic solution contains from five to fifty percent permethrin and between fifty and ninety millimeters of organic solution may be added to each liter of water.

Preferably, an insecticide loading of between four hundred and seven hundred milligrams per square meter is achieved by a wet pick-up of between fifty to seventy percent. Preferably, the insecticide is permethrin.

DETAILED DESCRIPTION OF THE PREFERRED EMBODIMENTS

The invention will now be described by way of example only with reference to the previously identified drawings.

Figure 1:
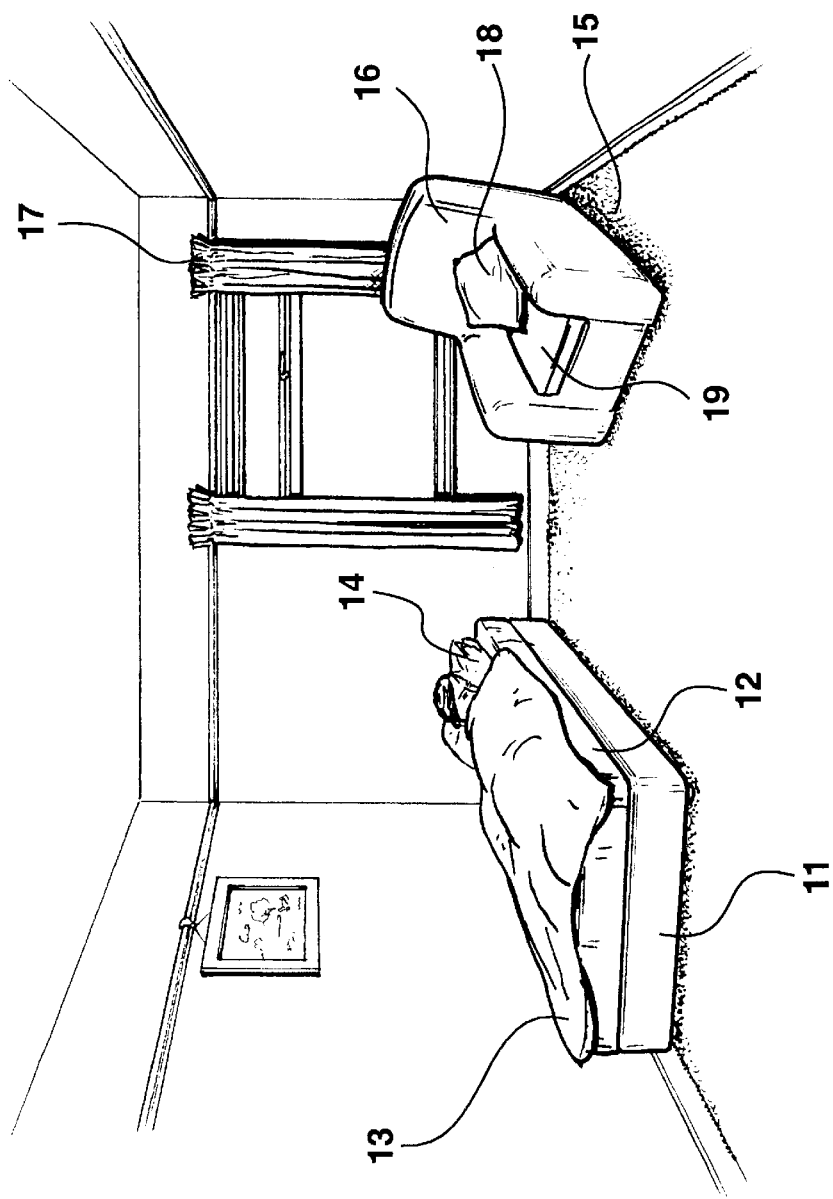
FIG. 1 shows a domestic environment including a number of articles of soft furnishing, including a mattress.

A domestic environment shown in FIG. 1 includes a bed 11 having a mattress 12 made up with a duvet 13 and pillows 14. The environment also includes a carpet 15, a chair 16 and curtains 17. The chair 16 has cushions 18 and 19 applied thereto. All of these articles of soft furnishing, including the carpet 15 and the curtains 17 provide suitable environments for populations of house dust mites. However, the presence of house dust mites are particularly annoying to allergenic sufferers when found in mattress 12, duvet 13, pillow 14, cushion 18 or cushion 19. Thus, in order to provide relief from these allergenic reactions, it is preferable to treat such items when an allergenic person would normally come into sustained contact with such items, particularly mattress 12, duvet 13 and pillow 14.

Figure 2:
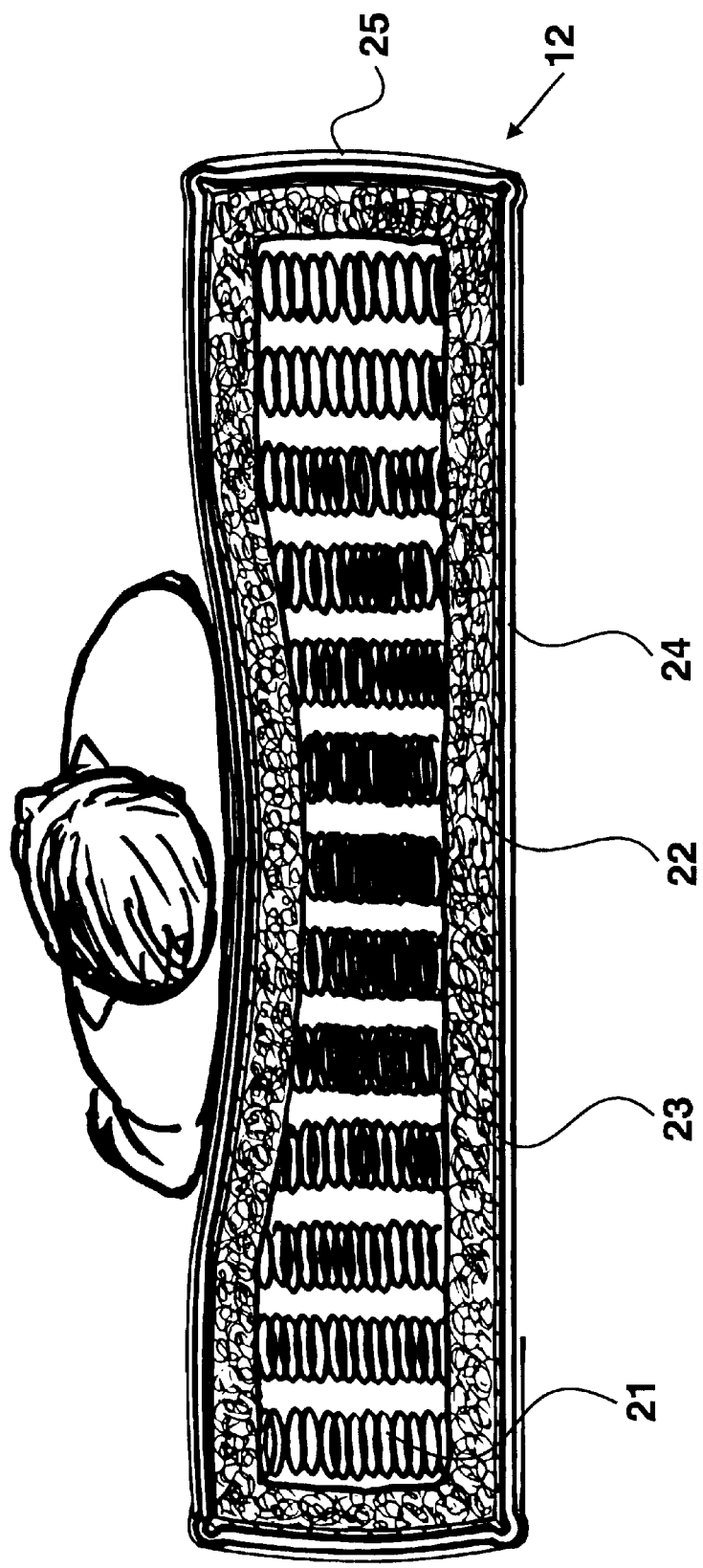
FIG. 2 shows a diagrammatic cross-section of the mattress identified in FIG. 1, surrounded by an impregnated cover.

Mattress 12 is detailed in FIG. 2. Mattress 12 is made up of a central core of springs 21 (or foam) surrounded by a layer of wadding 22, both encapsulated in a textile covering 23. House dust mite populations are often found in the layer of wadding 22, behind the textile cover 23. An insecticide impregnated covering 24 is placed around the mattress so as to totally enclose the top and sides of the mattress. After the mattress has been enclosed in this way, it may be used in a conventional fashion, possibly having a fitted sheet 25 applied thereto.

If after covering a mattress with an impregnated sheet, symptoms still persist, it may become necessary to take further action so as to reduce if not eliminate a sufferer's exposure to mite debris. In particular, similar covers may be placed over pillows, duvets and cushions etc. Preferably, the impregnated covering is applied directly to the duvet, cushion or pillow whereafter conventional coverings may be applied in the usual way. The objective is to bring the impregnated covering into a position which is as close as possible to the locations preferred by the mites; usually within soft wadding material that is displaced from the centre of such material and towards the source of heat, moisture and food created by the human occupants.

Previously, known impregnated coverings have been fabricated from a netting material, primarily because netting materials are familiar as insect barriers. Thus, for example, netting is often used as a physical barrier for mosquitoes. Furthermore, a covering made from a netting material is relatively lightweight and its presence would not be obvious when positioned between, say, a mattress and a conventional mattress covering or sheet. However, when impregnated with an insecticide, the material provides a different type of functionality to that provided by a mere physical barrier.

In the preferred embodiment, and as disclosed in international patent publication WO 96/28974, a preferred insecticide for the purpose of eliminating house dust mites is permethrin. Permethrin $C_{21}H_{20}CL_2O_3$ is an example of the class of chemicals identified as synthetic pyrethroids and other examples are deltamethrin, sypermethrin, allethrin and bifenthrin. If a house dust mite comes in to contact with a sufficient concentration of permethrin, the mite is killed and ultimately a colony of mites would be destroyed. Furthermore, weaker concentrations of permethrin can be detected by mites and as such the mites are deterred from initiating an infestation.

Further investigation on the part of the present applicants has been initiated, given that trials conducted using netting impregnated with permethrin provided protection against house dust mites for a period of time considerably less than that anticipated as a result of laboratory trials. Further investigation has shown that although a covering may contain sufficient permethrin to deter or even kill house dust mites, as concentrations decrease, house dust mites may still be attracted to surrounding soft furnishing. Thus, although the presence of a mattress cover may prevent house dust mites from coming close to the cover itself, as concentrations of permethrin in the cover are reduced, house dust mites may still invade the central core of the mattress and their debris may then result in allergenic reactions.

In laboratory conditions, a covering, possibly fabricated from netting, will retain permethrin within the interstices of the net with minimal permethrin loss. However, in a real domestic environment, personal movement results in the material being rubbed, sometimes against itself and sometimes against other soft furnishings, such as sheets, within the environment. This rubbing results in the permethrin being lost from the covering and as a result, over a period of time, the level of protection provided by the covering, reduces.

It may be thought that, in order to reproduce an environment similar to that in a laboratory, it would be preferable to provide a system in which the permethrin is permanently held within an appropriate covering such that its concentration does not decrease over a period of time due to physical movement. However, further investigations have shown that the release of permethrin from the covering and into the surrounding environment is an important factor in terms of destroying and resisting house dust mite infestation.

As permethrin is lost from the covering, due to physical movement, a quantity of permethrin will be absorbed by the mattress itself, thereby providing a level of protection through to the mattress core in addition to providing a level protection merely at the periphery. Thus, if a material is used which strongly resists the release of permethrin, even in response to vigorous physical movement, protection is provided for a long period of time but the degree of protection is reduced. Furthermore, increasing the initial dose of permethrin to the covering does not significantly improve the situation, given that permethrin is still retained by the covering and does not allow a significant degree of the insecticide to penetrate the mattress or other soft furnishing as a whole.

The present invention provides an improvement over previously known coverings impregnated with insecticide, in which the insecticide is released from the covering over an operational period so as to encourage the absorption of the insecticide into the soft furnishing. In order to achieve the desired degree of absorption, the covering is manufactured from a machined fabric having interstices sufficiently small to reduce the rate of insecticide release over the operational period. In particular, a covering is used that has interstices that are significantly smaller than that provided by machined netting. In a preferred covering, a knitted voile fabric is used of the type shown in FIG. 3.

Figure 3:
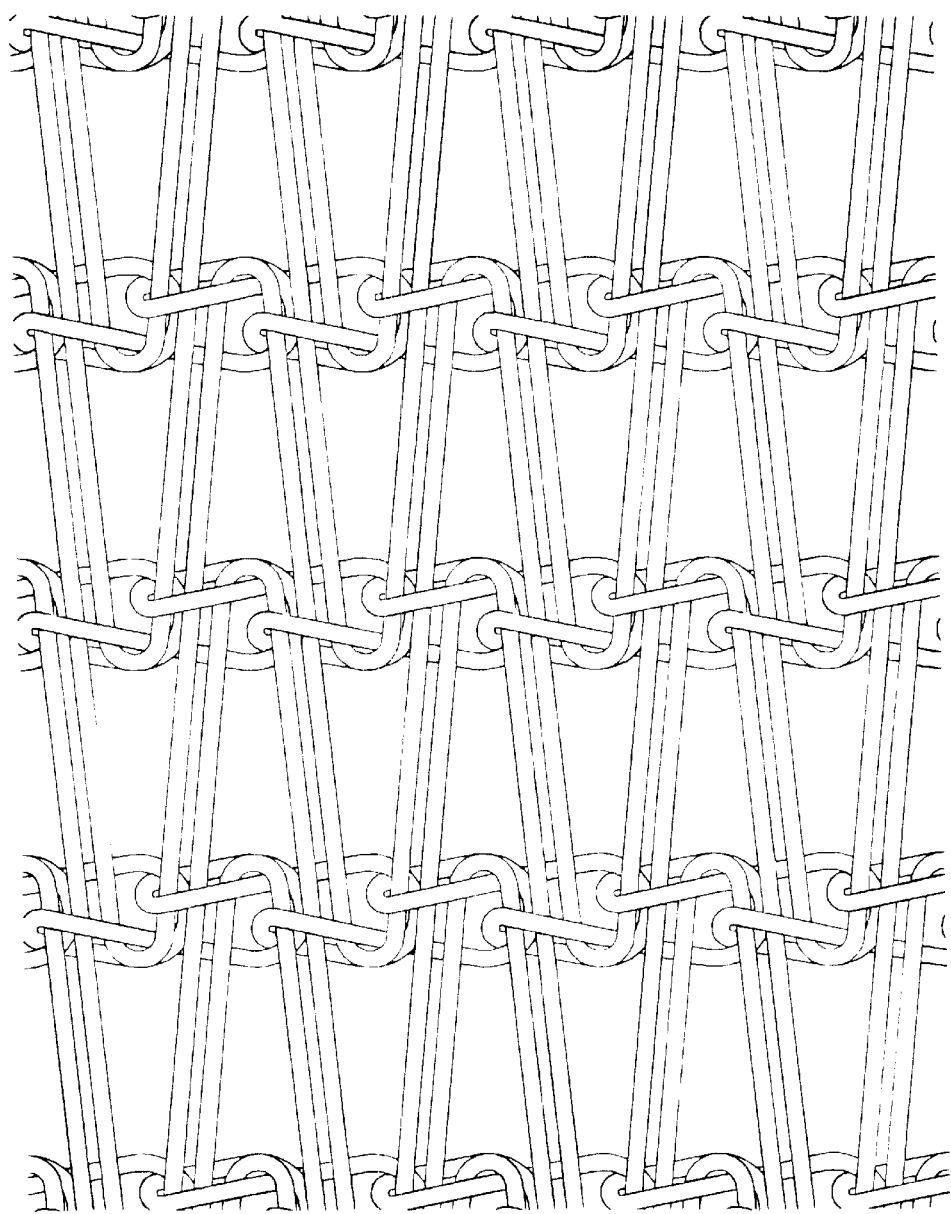
FIG. 3 illustrates a knitted voile representing a preferred fabric.

The knitted voile shown in FIG. 3 differs from conventional curtain voile, of the type used for decorative effect. The knitted voile shown in FIG. 3 is slightly denser, that is to say, less transparent and more stable, than conventional curtain voile although it is made on a warp knitting machine of similar construction to that used for the production of curtain voile. However, whereas the production of curtain voile requires three guide bars, the construction shown in FIG. 3 requires only two guide bars. It is particularly suitable for the purpose proposed due to its larger fibre surface area, resulting in interstices of a preferred size for retaining the permethrin for a long operational period, when compared to netting, while at the same time allowing a degree of permethrin release when stimulated by physical activity. Furthermore, the knitted voile presents interstices of more complex shape, when compared to netting, further enhancing its properties in terms of holding permethrin while allowing a controlled release of the insecticide over a period of time.

Voile of the type shown in FIG. 3 and similar type voiles used for curtaining etc are described in "Knitting Technology" by David J. Spencer published by Woodhead Publishing Limited (ISBN 1 85573 3137).

The knitted voile shown in FIG. 3 shall be identified as PHC voile, to distinguish it from the type preferably used in the manufacture of curtains. It is knitted from continuous filament polyester, ensuring that the permethrin is held between the knitted yarns and is not absorbed by the yarns themselves. When knitted to provide a similar feel to an equivalent netting, the size of the yarn itself is relatively smaller but the actual knitting pattern, as shown in FIG. 3, is considerably more complex such that, once knitted, the overall weight per unit area and hence the overall quantity of polyester within the cover, is substantially similar.

A mattress cover of the type shown in FIG. 2, fabricated from a PHC voile of the type shown in FIG. 3, should provide protection against house dust mites and other insects for a period of two years. The cover is designed to provide protection for a period of two years, given that a user would normally wish to replace such a covering after a period of time, thus allowing the original dose of permethrin to be kept relatively modest and thereby harmless to people coming into contact with the covering. Over this period of two years, dust mites in the vicinity will be killed and larger insects will tend to be repelled by the presence of the permethrin, which in itself would eliminate the possibility of an article becoming infested. However, any insects coming into contact with the cover directly would be killed.

In use, abrasion will cause permethrin to be lost from the covering, thereby allowing the insecticide to steep into the mattress covering 23 and into top layers of mattress wadding 22. In this way, a reservoir of permethrin is provided within the mattress itself, thereby extending the range over which mites are killed and other insects are repelled. Thus, over a preferred operational period of two years, the loss of permethrin from the covering in this way enhances the overall effectiveness of the covering and the PHC voile ensures that the rate of permethrin loss is optimised, as illustrated in FIGS. 4A, 4B and 4C.

Figure 4A:
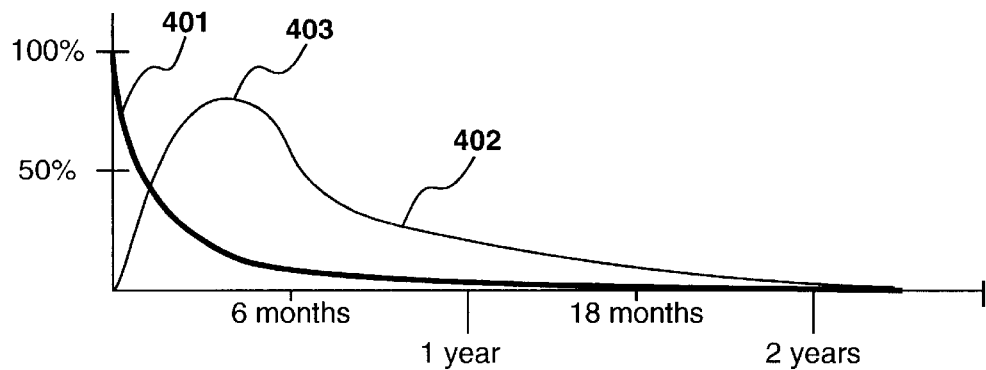
FIGS. 4A, 4B and 4C illustrate rates of permethrin loss for different types of material.
Figure 4B:
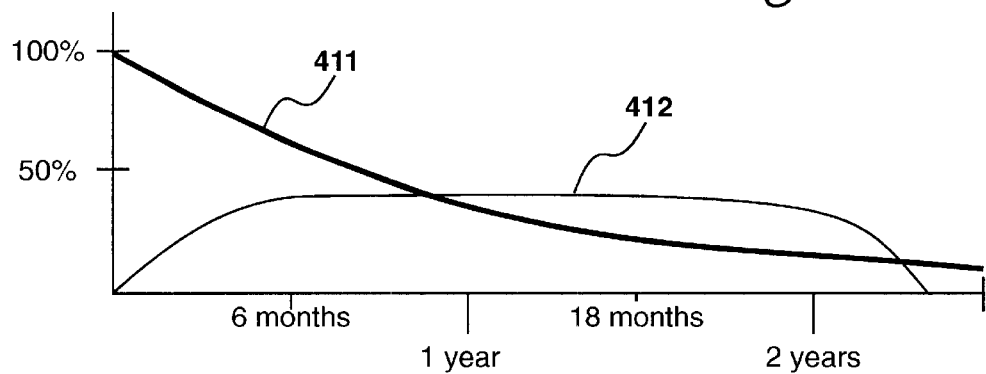
Figure 4C:
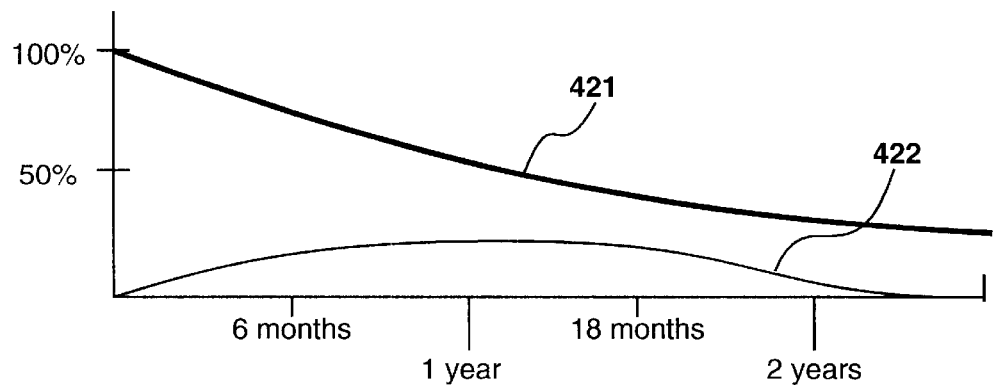

Each of the three graphs shown in FIGS. 4A to 4C illustrate the loss of permethrin from respective cover types over a preferred operational period of two years. Each covering is provided with a substantially similar dose of permethrin, identified as one hundred percent, which, over the operational period, is lost from a mattress cover, primarily through steeping into the underlying mattress.

FIG. 4A shows a situation in which a conventional netting material, such as sandfly netting, is used, as suggested in the previously identified international patent publication. The loss of permethrin substantially follows an exponential decay 401 and this loss of permethrin over the operational period results in a build-up of permethrin within the underlying mattress, indicated by curve 402. Curve 401 drops off sharply such that the degree of permethrin available within the environment has reduced significantly after six months of use. The degree of permethrin available within the mattress, by the steeping progress, increases rapidly over an initial period and reaches a peak 403 after about four months. Thereafter, as the rate of permethrin loss from the cover tails off, the insecticide is lost from the underlying mattress at a rate greater than that by which it is received from the cover, such that, as illustrated by curve 402, the amount of permethrin within the mattress decreases. Thus, experiments have shown that in order for the level of permethrin contained within the mattress to remain substantially constant, a continual steeping or feeding from the overlying cover is required over a period of time.

Conventional systems have lost most of their permethrin from the cover after six months of use but continue to provide protection as a result of permethrin retained within the mattress itself. However, after a one year period, much of the permethrin has been lost from the mattress and after eighteen months virtually all of the permethrin has been lost, such that over the period from eighteen months to two years, virtually no protection is available. Using a covering of this type, it would be necessary to replace the covering at one yearly intervals in order to provide continuous protection. Furthermore, a substantial proportion of the permethrin is lost over an initial two month period which could result in ambient concentrations of the chemical that are higher than preferred maximums.

As the permethrin is absorbed by the mattress, its concentration is diluted. Thus, the permethrin continues to steep through the mattress but ultimately if the mattress holding permethrin is not continually topped up, the overall concentration will drop below an effective level. Furthermore, permethrin breakdown occurs due to natural processes such that a continual supply of the chemical is required in order to achieve the pesticide effect.

The situation for the PHC voile, shown in FIG. 3, is illustrated in FIG. 4B. PHC voile is provided with a substantially similar concentration but, as illustrated by curve 411, the rate of permethrin loss is significantly less such that a significant degree of permethrin is still available within the cover after the two year operational period. However, as required, there is a loss of permethrin from the cover resulting in a build-up of permethrin within the underlying mattress. Mattress concentrations are illustrated by curve 412 which, as shown, reaches a maximum level after about four months whereafter the concentration remains substantially constant just before the two year operational end. It can therefore be seen that by using PHC voile instead of netting, the rate of loss from the cover balances the rate of loss from the mattress such that, over most of the operational period, the mattress concentration remains substantially constant. Furthermore, the slower permethrin loss ensures that ambient concentrations are minimised, thus avoiding a permethrin high point as illustrated by peak 403 in FIG. 4A.

The PHC voile provides interstices sufficiently small to reduce the rate of insecticide release over the operational period. Other materials may be employed which have even smaller interstices, such that the insecticide is held more firmly by the material, resulting in an even slower insecticide release rate over the operational period. In some circumstances, such a material may be considered preferable if a lower rate of permethrin loss is required. However, as illustrated in FIG. 4C, this may not always be desirable, given that it may result in the concentration of permethrin held by co-operating structures, such as mattress 12, failing to reach optimum concentrations.

The response shown in FIG. 4C was developed from the use of a reverse lock-knit fabric or similar close-knitted fabric as described in "Knitting Technology". The reverse lock-knit fabric receives a substantially similar concentration of permethrin to the sandfly net shown in FIG. 4A and to the PHC voile shown in FIG. 4B. Under similar operational conditions, the rate of permethrin loss is significantly reduced, as illustrated by curve 421. Although the rate of loss is reduced, there is some permethrin loss, resulting in permethrin concentrations within the mattress 12 increasing, as illustrated by curve 422. However, if it is assumed that a concentration of permethrin to the extent defined by curve 412 is required, in order to provide optimum effect, it can be seen that the concentration provided by curve 422 fails to reach the required extent and as such the overall performance of the material is less than ideal.

If it is assumed that, in accordance with standard hygiene practice, the cover is replaced at two yearly intervals, a significant proportion of the permethrin would be retained within the cover and therefore not used for the purpose for which it was intended. Thus, in many systems there is an optimum balance, requiring a material which retains the permethrin to a degree while allowing a predetermined release rate so as to ensure that permethrin is present within the cover itself over the operational period while at the same time allowing a degree of permethrin to build-up in surrounding structures over the operational period, such that house dust mites and similar insects are killed by the cover itself and are repelled from the surrounding structures.

Many material structures are known and, in the production of the overall configuration, many variables may be adjusted in order to achieve the required result. The essential feature of the present invention is that the fabric is machined so as to have interstices sufficiently small to reduce the rate of insecticide release over a defined operational period. In the present preferred embodiment, the cover is required to remain operational for at least a period of two years and the rate of release is required to be sufficient so as to provide a sufficient concentration of permethrin within an underlying mattress.

In addition to being released into mattresses, the permethrin would also be released into overlying sheets. Permethrin concentration in sheets provides additional protection but given that the sheets would tend to be changed regularly, it is not possible for significant levels of the insecticide to build-up to an extent similar to the build-up of insecticide in the mattress.

| | |
|---|---|
| Yarn type: | Continuous filament polyester thirty-three decitex |
| Fabric Type: | Warp knitted PHC voile (FIG. 3) |
| Knitting machine type: | Twenty-eight gauge tricot warp knitting machine with two guide bars, both fully threaded. Yard feed run-in front guide bar six hundred and sixty-five millimeters per rack back guide bar, nine hundred and ninety-eight millimeters per rack. Pattern chain construction front guide bar 1-0/0-1/ and back guide bar 0-0/3-3/ |
| Knitted quality courses per centimeter: | Twenty nine point three |
| Whales per centimeter: | 11.0 |
| Construction: | Front guide bar chain stitch on one needle Back guide bar laying in over three needles. |
| Resulting fabric weight: | Forty-one grams per square meter. |

PHC voile is knitted as specified above and then tailored into appropriate coverings for mattresses, pillows or other soft furnishings. The tailored coverings are then processed to provide five hundred and fifty milligrams of permethrin per square meter, and field trials have shown that a mattress cover of the type shown in FIG. 2 continues to be fully operational until a concentration of one hundred and seventy-six milligrams per square meter has been reached. Thus, the PHC voile is constructed to provide a rate of permethrin loss such that, over the operational period of two years, the permethrin concentration has reduced from five hundred and fifty milligrams per square meter to approximately one hundred and seventy-six milligrams per square meter.

Figure 5:
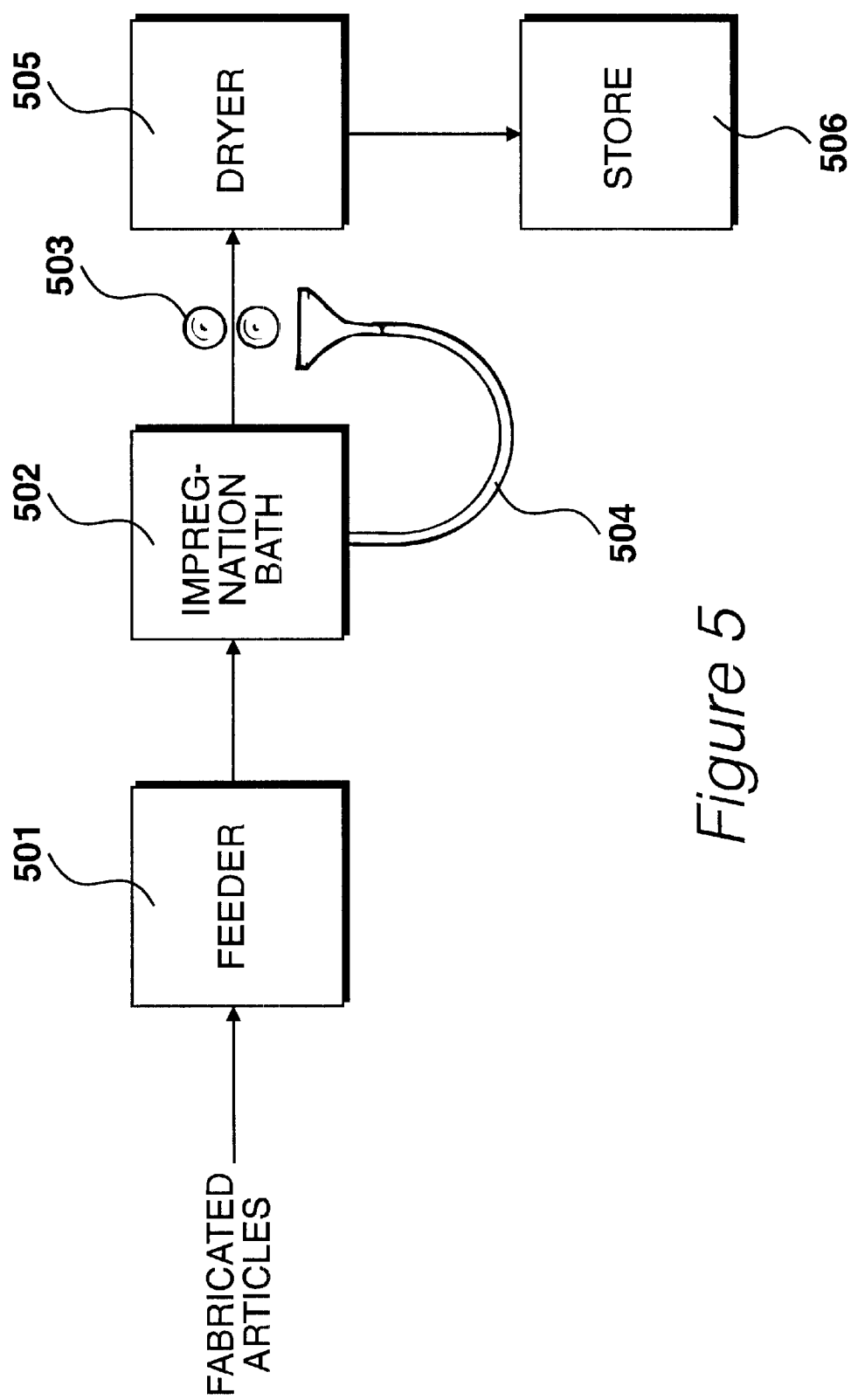
FIG. 5 illustrates a permethrin impregnation process.

The permethrin impregnation process is illustrated in FIG. 5. Fabricated articles are placed into a feeder 501 such that, in a controlled manner, the articles are introduced to an impregnation bath 502. After passing through the impregnation bath, the articles are transported through a set of rollers 503 to remove excess impregnation fluid, which is returned to the impregnation bath by a fluid return 504. After being rolled by rollers 503, the articles move into a continuous dryer 505, configured to dry the articles such that solvent is removed from the fibres and the permethrin insecticide is retained by the fibres and held by the interstices of the material. From the dryer 505, the articles are transferred to a store 506, arranged in a controlled temperature and humidity environment.

Impregnation bath 502 is constantly stirred with low sheer continuous paddle stirrers to maintain an even distribution of permethrin within the solution. The temperature of dryer 505 should not exceed one hundred and ten degrees Celsius and is preferably maintained at an optimum working temperature of eighty degrees Celsius.

Permethrin, also identified as FMC 33297 and by several other chemical names, is present as two isomers, the relative concentrations of which would be specified in any particular batch. Permethrin is hydrophobic and does not dissolve in water but can be suspended in water as an emulsion. To facilitate its suspension in water, permethrin is usually obtained in organic solution, with surfactants; an example being sold under the trade mark Dragnet having a permethrin concentration of thirty-six point eight percent.

The detailed example described herein makes reference to the use of the organic solution distributed under the name "Dragnet". An alternative solution is distributed by "AgrEvo" under the trade mark Permanone. Permanone is available with permethrin concentrations of forty percent or ten percent, thus, when formulating a suspension for dipping purposes, water concentrations should be modified accordingly in order to produce a fluid of the required permethrin concentration.

It is possible for articles impregnated by the process shown in FIG. 5 to be recycled. Thus, returned fabrics may be applied to feed 501 and a re-impregnation process may be performed, substantially similar to an initial impregnation process.

Covers such as mattress covers are preferably configured entirely from the PHC voile. However, particularly in alternative configurations, the cover may include portions fabricated from other materials and the combination, including partial PHC voile and partial non-optimum fabric, may be applied to the process shown in FIG. 5. Composite materials of this type may be fully impregnated by the process shown in FIG. 5 or, alternatively, only portions of the composite may be impregnated. An encapsulating covering may be applied to the composite so as to protect it from the impregnation process in portions where such an impregnation is not required and would be considered undesirable.

The concentration of permethrin retained by coverings fabricated from machine knitted PHC voile may be controlled by two factors. Firstly, it is determined by the concentration of the chemical in the impregnation bath 502 and secondly it is determined by the amount of liquid retained by the fabric prior to being applied to dryer 505. Thus, the mangling operation performed by rollers 503 is an important aspect of the overall procedure, in order to obtain the required level of chemical concentration. The procedure of wetting the material followed by a process of removing surplus solution is referred to as wadding and the pressure applied by rollers 503 controls the amount of moisture retained in the textile material, usually referred to as the wet pick-up. Thereafter, the active chemical is retained within the fabric while its carrying liquid is evaporated during the drying process.

Wet pick-up is usually expressed as a percentage of the dry textile weight, such that the percentage wet pick-up equals the weight of liquid retained after impregnation divided by the dry weight and multiplied by one hundred. In this way, the loading of the chemical product (permethrin in this example) from the impregnating liquor depends upon the relationship between the wet pick-up and the liquor concentration.

It is usual to operate impregnation equipment to provide a consistent and known wet pick-up for any given textile product type. Different chemical loading can then be obtained by varying the concentration of the chemical agent in the impregnating liquor.

Polyester fibres are not capable of absorbing significant amounts of water, therefore the aqueous liquor retained by the fabric is present as a surface layer. This in turn ensures that the permethrin is held between the interstices of the weave and not within the polyester fibres themselves.

The preferred permethrin loading is five hundred and fifty milligrams per square meter and this is achieved by means of a wet pick-up of sixty-five percent using an aqueous dispersion containing sixty-four milliliters of Dragnet concentrate per liter of water.

What I claim is:

1. A covering for fabric-coated furnishings, impregnated with permethrin with a loading of between five hundred and six hundred milligrams per square metre and configured to release permethrin over an operational period of between one-and-a-half and two-and-a-half years to give a final loading of between one hundred to two hundred milligrams per square metre, the covering being from a polyester yarn having a gauge in the range of twenty to one hundred decitex, wherein said covering is fabricated totally or in part of a knitted voile.

2. The covering according to claim 1, configured to be applied to mattresses, duvets, pillows, cushions, pet beds, or other bedding elements.

3. The covering according to claim 1, wherein said knitted voile is machined on a warp knotting machine with two guide bars to provide a voile denser than curtain voile.

4. The covering according to claim 1, wherein said voile has between twenty-five to thirty-five courses per centimeter and between eight to fifteen whales per centimeter.

5. The covering according to claim 1, wherein the voile has a weight of between thirty-five to forty-five grams per square meter.

6. The covering according to claim 1, wherein said voile is knitted from polyester yarn.

* * * * *